United States Patent [19]

McComb

[11] Patent Number: 5,349,946
[45] Date of Patent: Sep. 27, 1994

[54] MICROPROCESSOR CONTROLLED FLOW REGULATED MOLECULAR HUMIDIFIER

[76] Inventor: R. Carter McComb, 30 Kenwood Pkwy., St. Paul, Minn. 55105

[21] Appl. No.: 958,031

[22] Filed: Oct. 7, 1992

[51] Int. Cl.$^5$ ............................................. A61M 15/00
[52] U.S. Cl. ........................... 128/203.17; 128/203.12; 128/204.17
[58] Field of Search ...................... 128/203.12, 203.17, 128/203.27, 204.17, 203.16

[56] References Cited

U.S. PATENT DOCUMENTS

| | | | |
|---|---|---|---|
| 4,028,445 | 6/1977 | Hickmann et al. | 128/203.27 |
| 4,110,419 | 8/1978 | Miller | 128/203.27 |
| 4,219,725 | 8/1980 | Groninger | 128/203.27 |
| 4,303,601 | 12/1981 | Grimm et al. | 128/203.27 |
| 4,481,944 | 11/1984 | Bunnell | 128/203.17 |
| 4,621,632 | 11/1986 | Bartels et al. | 128/203.27 |
| 4,621,633 | 11/1986 | Bowles et al. | 128/203.17 |
| 4,708,831 | 11/1987 | Elsworth et al. | 128/203.27 |
| 4,770,168 | 9/1988 | Rusz et al. | 128/203.27 |
| 5,006,109 | 4/1991 | Douglas et al. | 604/26 |
| 5,101,820 | 4/1992 | Christopher | 128/203.26 |
| 5,172,686 | 12/1992 | Anthony | 128/204.17 |

OTHER PUBLICATIONS

"Effects of Humidity in Inspired Air on Airway Resistance and Functional Residual Capacity in Patients with Respiratory Diseases", by W. T. Josenhans et al., Respiration 26 at 435–443 (1969).
"Circuit Temperature Fails to Predict Humidity" by Gilmour I. J. FCCP et al. University of Minnesota.
"Humidifiers Kill Bacteria" by I. J. Gilmour M.D. et al.
"Researchers Find Routine Vent Tubing Changes a Costly Ritual" from Hospital Infection Control newsletter vol. 19, No. 9 at 113 (Sep. 1992).
"Ventilators, High Frequency [15-783]" and Ventilators, Time Cycled [14-361] from Technology for Respiratory Therapy (1991).
"A Method to Maintain 7-Day, Bacteria-Free Continuous Ventilator Circuits" by Richard Radford MBA RRT, Eric Anderson BS RRT and Levels of Contamination of Ventilator Circuits: A Comparison at 48 Hours and 12 Hours by Michael J. Mahlmesiter MS RRT RCPT et al., Respiratory Care vol. 32, No. 10 at 942 (Oct. 1987).
Hospital Infection Control newsletter, vol. 20, No. 2, at 103.
"Nosocomial Pneumonia and Cascade Humidifiers" by Michael McPeck BS RRT and Humidifier Nemenclature by Donald E. Craven M.D. and Kathleen A. Steger RN MPH from Respiratory Care, Sep. 1989, vol. 34, No. 9.
"Pathogenesis and Prevention of Nosocomial Pneumonia in the Mechanically Ventilated Patient" by Donald E. Craven M.D. et al. from Respiratory Care, Feb. 1989, vol. 3, No. 2.
"Contaminated Condensate in Mechanical Ventilator Circuits" by Donald E. Craven et al., Concise Clinical Study (1983).
"Prospective Study of Nosocomial Pneumonia and of Patient and Circuit Colonization During Mechanical Ventilation with Circuit Changes Every 48 Hours Versus No changes" by Dider Dreyfus et al. (1990).

(List continued on next page.)

*Primary Examiner*—Edgar S. Burr
*Assistant Examiner*—Aaron J. Lewis
*Attorney, Agent, or Firm*—Kinney & Lange

[57] ABSTRACT

A humidification system humidifies breathable gas that is supplied to a patient with a ventilator or an anesthesia circuit having inhalation tubing connecting from the ventilator to the patient and exhalation tubing extending from the patient. The humidification system includes a blotting paper humidifier disposed in the inhalation tubing adjacent to the patient. Piping carries an amount of water from a reservoir to the humidifier, and the amount of water delivered to the humidifier is limited by a controllable pulsing valve disposed in the piping. A measurement device measures at least two parameters, and a regulation device regulates the pulsing valve as a function of the measured parameters so that an appropriate amount of water is delivered to the blotting paper to achieve a desired humidity level in the gas.

22 Claims, 5 Drawing Sheets

OTHER PUBLICATIONS

"Bubbling Humidifiers Produce Microaerosols Which Can Carry Bacteria" by Frank S. Rhame M.D. et al. from Infection Control. 1986/vol. 7, No. 8.

"Contamination of Mechanical Ventilators with Tubing Changes Every 24 or 48 Hours" by Donald E. Craven M.D. et al. from the New England Journal of Medicine, vol. 306, No. 25, Jun. 24, 1982.

Search Results 1-6, "Nosocomial Pneumonia: New Concepts . . . "; Nosocomial Pneumonia in the Intubated Patient; Nosocomial Pneumonia in Intubated Patient Given Sucralfate . . . ; Bacterial Infections in Adult . . . ; Risk Factors for Pneumonia . . . ; Contaminated Medication Nebulizers . . . ; Contaminated Condensate in Mechanical . . . , all by D. E. Craven.

"A Method of Maintaining Sterility of Heated Humidifiers in Mechanical Ventilator Breathing Circuits" by Robert S. Deane, MB, Bch et al. Critical Care Medicine (1978).

"The Relationship Between Frequency of Ventilator Circuit Changes and Infectious Hazard" by Suzanne C. Lareau et al., American Review of Respiratory Disease, vol. 118 (1978).

"Work of Breathing During Pressure . . . " by J. W. Kreit; The Work of Spontaneous . . . by J. D. Truwit et al.; Imposed Work of Breathing . . . by R. M. Kacmarek et al.; and The Extra-Work of Breathing . . . by L. Brochard et al.

"A Method for Studying . . . " by P. Levy et al.; Inversed Ration Ventilation . . . by Jens B. Anderson; Effect of Continuous . . . by B. Petrof et al.; and The Use of Biofeedback to . . . by J. E. Holiday and T. M. Hyers.

"Disposable Condenser Humidifiers in Intensive Care" by T. E. Oh et al. from Anaesthesia and Intensive Care, vol. IX, No. 4, Nov. 1981.

"The Effects on Sputum Characteristics of Combining an Unheated Humidifier with a Heat-Moisture Exchanging Filter" by Masayuki Suzukawa M.D. et al. from Respiratory Care, Nov. 1989, vol. 34, No. 11.

"Efficacy of a New Hygroscopic Condenser Humidifier" by Rosemary Hay M.D. and Warren C. Miller M.D., Critical Care Medicine, vol. 10, No. 1 at 49 (1982).

"Humidification of Rapidly Flowing Gas" by Thomas J. Poulton M.D. and John B. Downs M.D., FCCP, Critical Care Medicine, vol. 9, No. 1 at 59 (1981).

"Cascade Humidifiers Produce Aerosols" F. Rhame (1983).

Abstracts of the 1989 ICAAC, p. 203.

"Studies of a New Humidifying Device as a Potential Source of Bacterial Aerosols" by Tom Schulze et al.

"Bacterial Contamination of Aerosols" by Alan K. Pierce M.D. and Jay P. Sanford M.D. from Arch. Intern. Med./vol. 131, Jan. 1973.

"An Evaluation of Bacterial Contamination of Ventilator Humidifying Systems" by Timothy M. Harris M.D. et al. from Chest, vol. 63, No. 6, Jun. 1973.

"The Potential Role of Inhalation Therapy Equipment in Nosocomial Pulmonary Infection" by James Allen Reinarz et al. from Journal of Clinical Investigation, vol. 44, No. 5, 1965.

"Bacteial Contamination Potential of Sterile, Prefilled Humidifiers and Nebulizer Reservoirs" by Joe A. Koss MS RRT et al. Heart & Lung, vol. 8, No. 6 at 1117 (1979).

"Guideline for Prevention of Nosocomial Pneumonia" by Bryan P. Simmons M.D. and Edward S. Wong M.D.

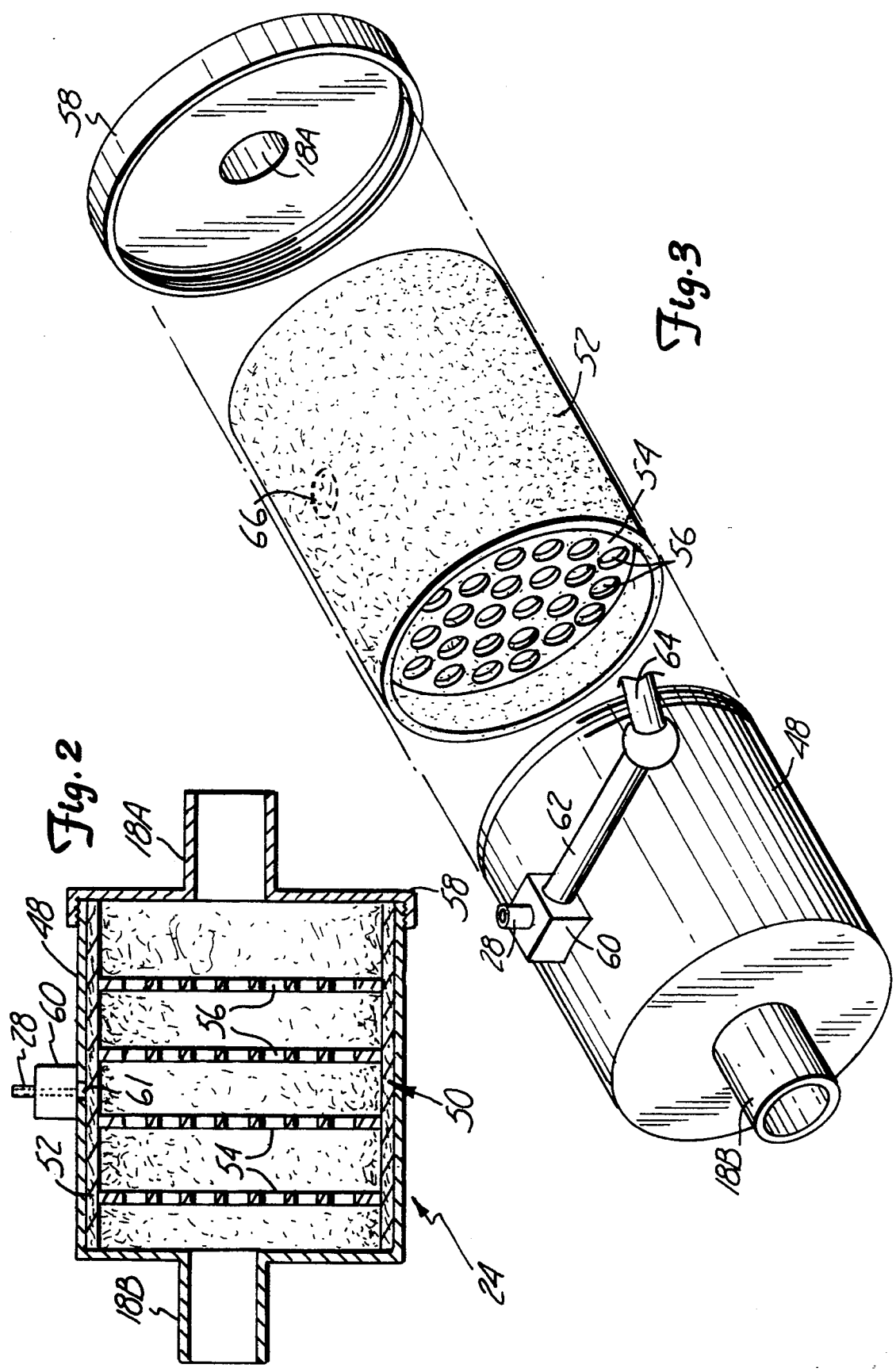

MICROPROCESSOR CONTROLLED FLOW REGULATED MOLECULAR HUMIDIFIER

BACKGROUND OF THE INVENTION

The invention relates generally to humidifiers, and, in particular, to humidifiers used in conjunction with a medical gas delivery device such as a ventilator.

Hospitals commonly provide a supply of breathable gas from an artificial respirator or ventilator to patients for various medical reasons. It is preferable to control both the relative humidity and the temperature of the gas being delivered to the patient. More particularly, humidification requirements typically consist of between 28 and 31 mg/$H_2O$/L gas at 37° C. which minimizes the drying out of the mucous membranes located in the patient's respiratory track. Thus, humidification lessens the chance of injury to delicate tissues and reduces the possibility of an obstruction in a patient's breathing passage as a consequence of insufficient mucous flow.

The medical industry produces two basic types of humidifiers. A first type of humidifier increases the relative humidity of a ventilator circuit in relationship to temperature and produces particulate water droplets or water vapor. A second type of humidifier increases the relative humidity of a ventilator circuit and attempts to produce only molecular humidity. A humidifier that produces molecular humidity without particulate water droplets is preferred to reduce nosocomial infections attributed to humidifiers that produce particulate water droplets such as nosocomial pneumonia. The second type of humidifier is currently implemented in the medical industry with a cascade humidifier which sends gas bubbles through water to produce molecular humidity, but also introduces particulate water droplets or water vapor in the humidified gas.

The Bartels et al U.S. Pat. No. 4,621,632 discloses a humidifier system which utilizes a heater assembly and microprocessor-based control circuitry. The humidifier chamber includes a continuous spiral heat exchange path which extends between a vapor storage chamber and an outlet of a humidifier chamber at which an air heating tube is connected, so that the outgoing air can be delivered to the patient. The microprocessor control circuitry includes a pair of sensors which are responsive to the temperature of the outgoing humidified air at the humidifier chamber outlet and at the patent end of the heating tube. The temperatures sensed are used to control the energization of both the heater assembly and a heating element of a heating tubes to provide air to the patient at a predetermined temperature with minimal rainout.

The Bowles et al U.S. Pat. No. 4,621,633 discloses a portable heated oxygen system for use with hypothermia victims. The heated oxygen system includes a humidifier that is regulated to control the humidified gas outflow between 1 to 20 liters/minute. The system also includes electrical control circuitry for operating heaters for controlling warming of oxygen supplies for inhalation rewarming.

The Douglas et al U.S. Pat. No. 5,006,109 discloses a system for administering gas to a patient during endoscopic or medical procedures that regulates the temperature, pressure, and volumetric flow rate of the gas. The system comprises a temperature sensor, a pressure indicator, and volume flow meter which allows the physician continuous monitoring of the quantitative status of each of these physiological parameters. The system is capable of controlling the temperature, the pressure, and volumetric flow rate of the gas. The system includes an optional humidification system.

SUMMARY OF THE INVENTION

The present invention relates to a humidification system for humidifying breathable gas that is supplied to a patient with a ventilator or an anesthesia circuit. The ventilator has inhalation tubing connecting from the ventilator to the patient and exhalation tubing extending from the patient. The humidification system utilizes a humidifier which includes blotting paper and which is disposed in the inhalation tubing adjacent to the patient. The system further includes a reservoir of water and piping that carries an amount of water from the reservoir to the humidifier. A controllable pulsing valve is disposed in the piping between the reservoir and the humidifier and is capable of limiting the amount of water delivered to the humidifier. The system uses a measurement device to measure at least two parameters. A regulation device regulates the pulsing valve as a function of the measured parameters so that an appropriate amount of water is delivered to the blotting paper to achieve a desired humidity level in the gas.

In a preferred embodiment of the present invention, the measurement device includes both a temperature probe and a flow meter. The temperature probe measures the temperature of the gas delivered to the patient and is disposed in the inhalation tubing between the humidifier and the patient. The flow meter measures the flow rate of the gas supplied by the ventilator or the anesthesia circuit. The flow meter is preferably disposed in the inhalation tubing between the humidifier and the ventilator.

In the preferred embodiment of the present invention, the regulating device includes a microprocessor which receives a temperature measurement signal from the temperature probe and a rate of flow signal from the flow meter. The microprocessor controls the pulsing valve in response to the temperature and rate of flow signals and thereby controls the relative humidity of the gas delivered to the patient.

The humidification system of the present invention delivers molecular humidity substantially free of particulate water droplets. Moreover, the humidification system achieves a desired humidity level in the range from approximately 28 to approximately 31 mg $H_2O$/l gas at approximately 37° C.

BRIEF DESCRIPTION OF THE DRAWINGS

FIG. 2 is a cross-sectional side view of a humidifier of the humidification system of FIG. 1;

FIG. 3 is a perspective exploded view of the humidifier of FIG. 2;

DETAILED DESCRIPTION OF THE PREFERRED EMBODIMENTS

Figure 1:
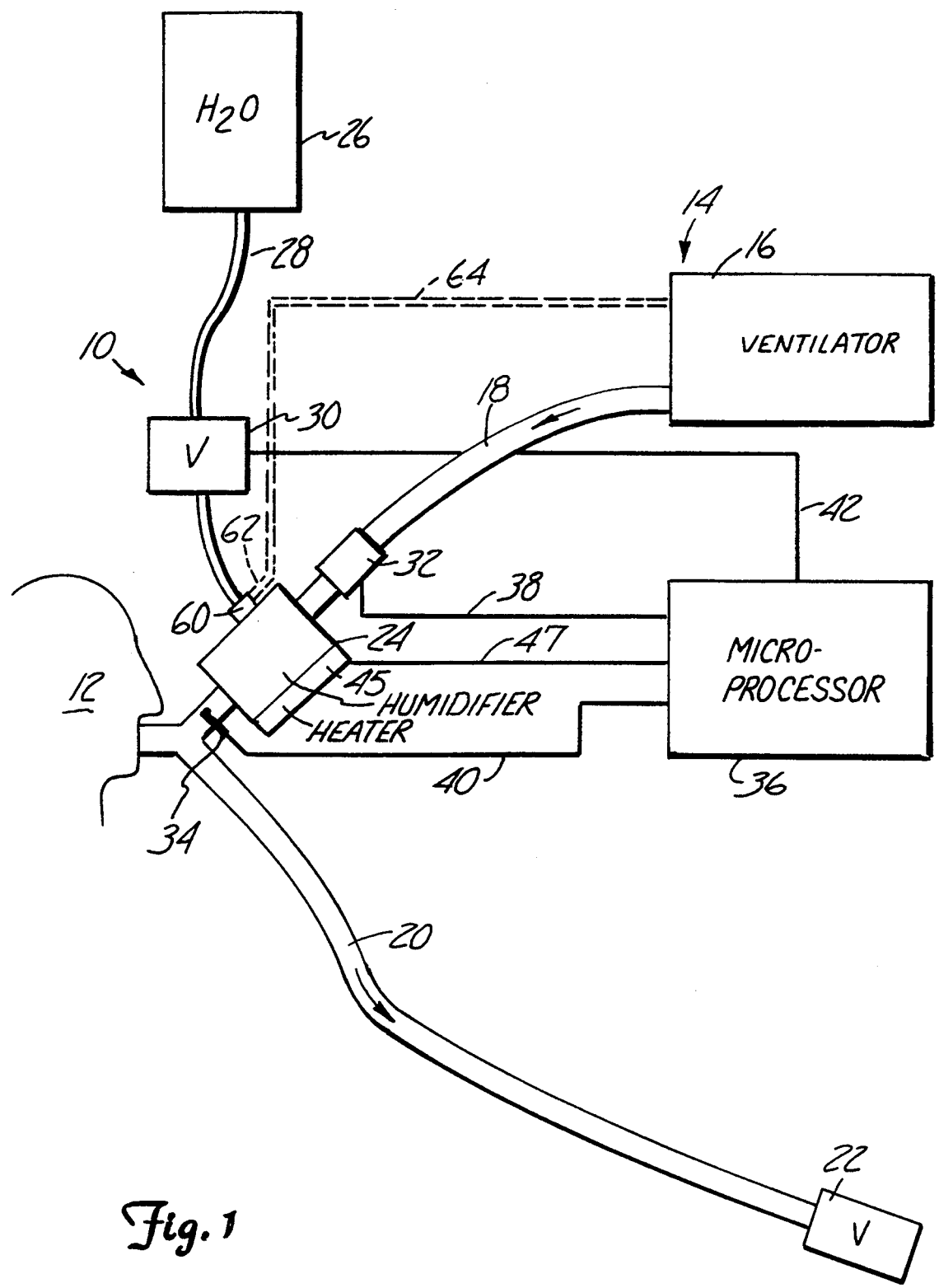
FIG. 1 is a block diagram of a humidification system according to the present; invention.

A humidification system is generally indicated at 10 in FIG. 1. The humidification system 10 is used to increase the relative humidity of breathable gas supplied to a patient 12 with a ventilator or anesthesia circuit generally indicated at 14. The ventilator circuit 14 includes a ventilator 16 which delivers breathable dry gas at a temperature approximately equal to body temperature or about 37° C. An inspiratory limb or inhalation tubing 18 connects the ventilator 16 to the mouth of a patient 12 through a suitable mask or other adapter and allows the gas from the ventilator to flow to the patient's mouth. Exhalation tubing 20 is included in the ventilator circuit to allow the patient to expel gas from the patient's lungs through an exhalation valve 22. Exhalation valve 22 is a standard check valve that allows air to flow from the patient outward and does not allow air to be sucked toward the patient through the valve when the patent is breathing inward.

The humidification system 10 includes a humidifier 24 which is disposed in the inhalation tubing 18 adjacent to the patient 12. A reservoir 26 is filled with water and is separated from humidifier 24. Piping 28 connects reservoir 26 to humidifier 24 and carries water from the reservoir to the humidifier. Typically, water flows from reservoir 26 to humidifier 24 because the reservoir is pressurized. A valve 30 which can be turned on and off in pulses is disposed in the piping 28 between reservoir 26 and humidifier 24. Pulsing valve 30 is controlled for limiting the amount of water delivered to humidifier 24 from reservoir 26.

A flow meter 32 is preferably disposed in inhalation tubing 18 between humidifier 24 and ventilator 16 adjacent to humidifier 24. Flow meter 32 outputs a flow signal representative of a flow rate of the gas supplied by the ventilator 16 into humidifier 24. A temperature probe 34 is preferably disposed between humidifier 24 and patient 12 and outputs a temperature signal representative of a temperature of the gas delivered to the patient from humidifier 24.

A microprocessor 36 is preferably used to control pulsing valve 30. Microprocessor 36 receives the temperature signal from temperature probe 34 indicating the temperature of the gas and the flow signal from the flow meter indicating the rate of flow of the gas. The flow signal is sent from flow meter 32 to microprocessor 36 via a line 38. The temperature signal is sent from temperature probe 34 to microprocessor 36 via a line 40. Pulsing valve 30 is controlled on or off by the microprocessor in response to these received signals representing the temperature out of the humidifier and the flow rate of gas into the humidifier via an algorithm that causes the microprocessor to calculate an amount of water that is needed to deliver a desired humidity level to the patient for a given rate of flow and temperature of the gas delivered to the patient. Because the gas exiting from ventilator 16 is dry, the algorithm is formulated from the fact that 32 mg $H_2O/l$ of gas at 37° C. delivers 100% relative humidity. Assuming that all of the water entering humidifier 24 is converted to molecular humidity, then the milligrams of water per minute that need to be delivered to the humidifier to achieve the desired humidity level in the gas delivered to the patient are easily calculated depending on the temperature of the gas flowing out of the humidifier and the liters per minute of gas flowing into the humidifier. Pulsing valve 30 allows a known amount of water to pass through pipe 28 to the humidifier with each pulse or opening of the valve. Therefore, a control signal representing the output of the algorithm is sent to pulsing valve 30 from microprocessor 36 via a line 42 to control the rate at which valve 30 is pulsed. Pulsing valve 30 turns on and off in response to these signals to maintain the water flow to the humidifier such that the desired humidity level is maintained. In this way, the relative humidity of the gas delivered to the patient is regulated.

In certain medical situations such as when administrating anesthesia to patient 12, the gas delivered to the patient may need to be heated to a higher temperature than that normally delivered by humidifier 24. Therefore, an optional heater 45 is added to humidification system 10 in a preferred embodiment of the present invention for heating humidifier 24 so that the temperature of the gas can be increased as the gas flows through the humidifier. Heater 45 can be turned on and off in response to a control signal from microprocessor 36 received via a line 47. The heater 45 provides added flexibility by allowing humidification system 10 to control both the relative humidity and the temperature of the gas being delivered to the patient.

The humidifier 24 is illustrated in more detail in FIGS. 2 and 3. Humidifier 24 comprises an outer housing 48 which is preferably constructed from plastic. A bat of blotting paper 50 or similar water absorbing material is disposed inside of housing 48. The bat 50 comprises an outer layer or sleeve of blotting paper 52. Outer layer 52 fits tightly around the inner periphery of housing 48 by constructing bat 52 to make the inner diameter of housing 48 match the outer diameter of layer 52. This forms a sleeve of blotting paper that fits in the housing. Bat 50 is also comprised of circular discs of blotting paper 54 layered inside of and on a plane perpendicular to outer layer 52. As indicated in FIG. 3, circular blotting paper rings 54 include holes 56 to allow gas to more freely flow through the humidifier. The discs 54 are spaced axially apart between the inlet and outlet. The blotting paper used in the construction of bat 50 to form the outer sleeve and cross discs is commercially available and is used in many humidifier systems.

As indicated in FIG. 2, tubing 18A which is connected to ventilator 16 is coupled to humidifier 24. Tubing 18B which is connected to provide breathable gas to the patient is coupled into the opposite (outlet) end of humidifier 24. The diameter of tubing 18 is substantially smaller than the diameter of the cylindrical humidifier 24. A threaded removable end cap 58 is provided on the inlet side of humidifier 24 providing access to the inside of humidifier 24. The bat of blotting paper 50 is easily removed from humidifier 24 and replaced by simply unscrewing cap 58 and slipping the sleeve 52 out of the housing 48.

Humidifier 24 is held in place with a housing 60 that is fixed to the humidifier housing 48 and also forms a support. Housing 60 is connected to an arm 62 which is in turn connected to coupling arm 64 which is connected to ventilator 16. This allows humidifier 24 to be held in place with an adaption from an existing clamping system on ventilator 16. As a result, humidifier 24 easily fits within a standard medical ventilator or anesthesia circuit.

When valve 30 is open, water from pressurized water reservoir 26 enters humidifier 24 through piping 28 to housing 60 on the top of humidifier 24 as indicated in FIGS. 2 and 3. The housing 60 has an interior chamber which opens at 61 to the interior of humidifier housing 48. As illustrated in FIG. 3, a contact region 66 indicates where water from reservoir 26 coming into housing 60 and through opening 61 actually makes contact with blotting paper 50. From this contact region, blotting paper 50 wicks the water to the entire sleeve 52 and to the discs 54 permitting all of the blotting paper to become substantially saturated with water. As respiratory gas flows through the discs 54 and adjacent the sleeve 52, the gas picks up moisture or is humidified. When blotting paper 50 is replaced or when the humidification system is started up, the pulsing value 30 is opened or pulsed a sufficient number of times to allow the blotting paper to become substantially saturated so that the rate of water into the humidifier will directly result in a proportional increase in the molecular humidity out of the humidifier.

As explained above, monitoring of the flow rate of the gas entering humidifier 24 with flow meter 32 and the temperature of the gas exiting humidifier 24 with temperature probe 34 enables microprocessor 36 to regulate pulsing valve 30 to control the amount of water delivered to humidifier 24 to only the amount that will produce a desired humidity level. The desired humidity level ranges from approximately 28 to approximately 31 mg $H_2O/l$ gas at approximately 37° C. As a result, the gas flowing through humidifier 24 only comes in contract with the substantially saturated blotting paper 50 which is unlike conventional humidifiers that allow gas to come in contact with a pool of water in a reservoir. Therefore, in the present invention, the humidifier delivers only molecular humidity which is substantially free of water droplets or water vapor because the gas does not come in contact with a pool of water. The desired humidity level is still reached because the appropriate amount of water is delivered to the substantially saturated blotting paper 50 via microprocessor control. Because substantially all of the water delivered to the humidifier is converted into molecular humidity, an increase in the rate at which the water is delivered directly increases the humidity of the gas.

Figure 4:
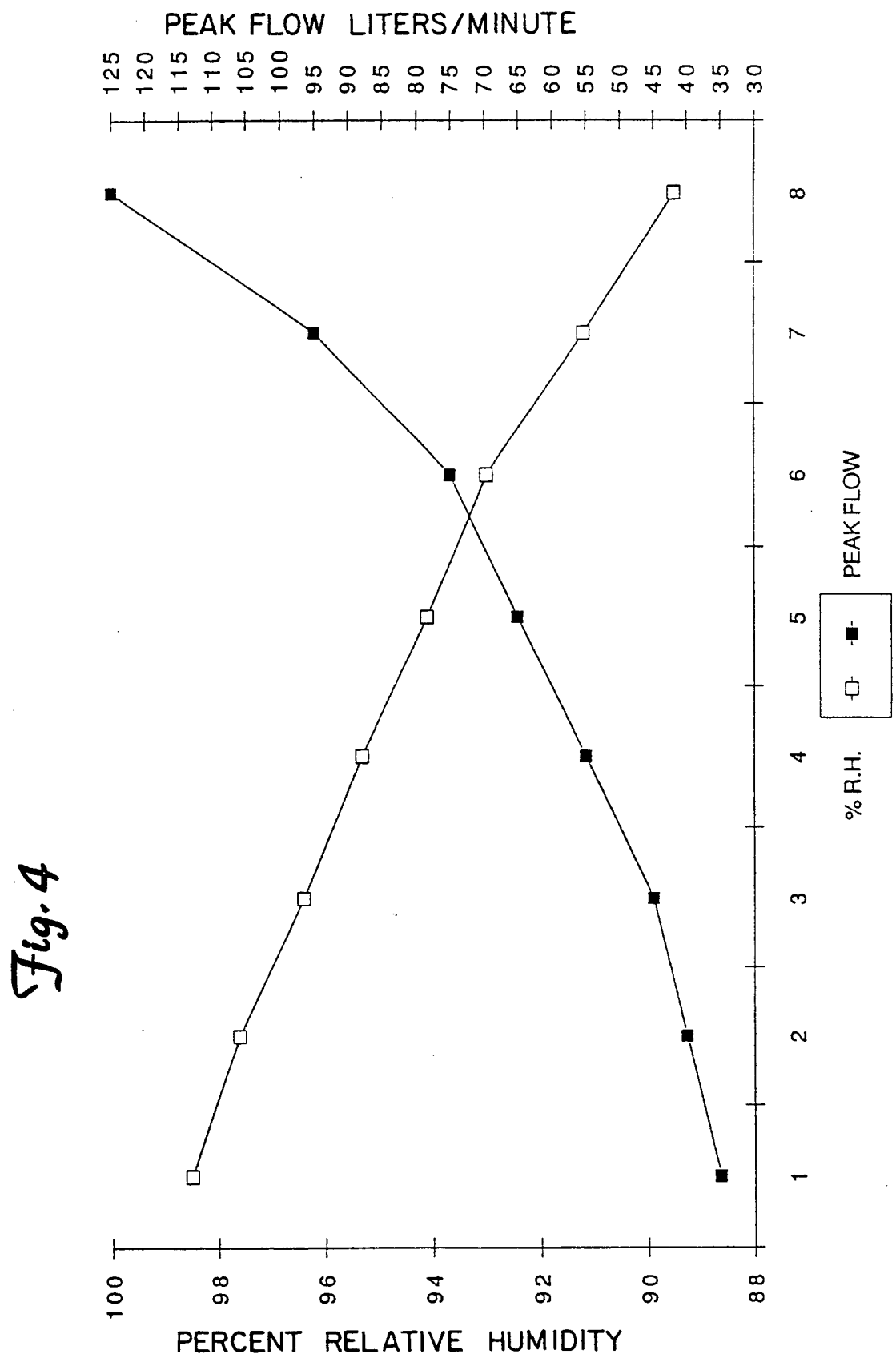
FIG. 4 is a graphical representation of percent relative humidity output from a prototype of the humidification system of FIG. 1 as a function of peak flow of a gas at a constant temperature.

Humidifier 24 is preferably designed to accept flow rates of between 2 and 150 liters/minute from the ventilator or anesthesia circuit. With an input flow rate of 2 to 150 liter/minute, humidifier 24 outputs gas to the patient with relative humidity in a range between 80 to 92% at body temperature (about 37° C). FIG. 4 illustrates, in graphical form, the percent relative humidity produced by a prototype of humidification system 10 for a constant temperature of gas at the humidifier output of between 33° C. to 35° C. at varying peak flow rates of gas delivered by ventilator 16. As the graph illustrates, even when peak flow of the gas reaches 125 liters/minute, the humidification system 10 delivers gas to the patient with nearly 90% relative humidity.

Figure 5:
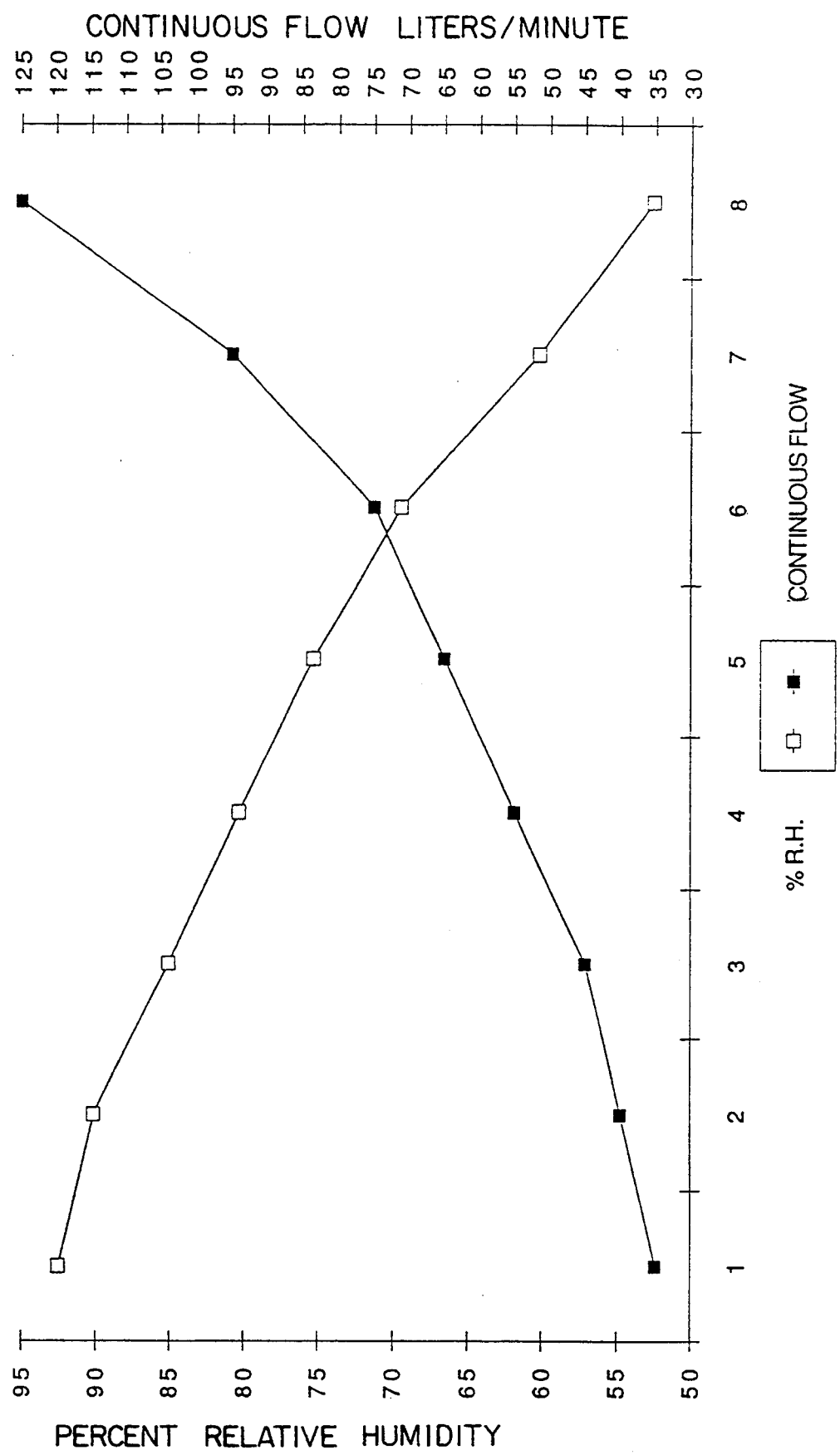
FIG. 5 is a graphical representation of percent relative humidity output from a prototype of the humidification system of FIG. 1 as a function of continuous flow of a gas at a constant temperature.

FIG. 5 illustrates a percentage of relative humidity of the gas delivered to the patient by the prototype of system 10 for a constant temperature of gas at the humidifier output of between 33° C. to 35° C. but is graphed in relationship to varying continuous flow rates of gas from ventilator 16. As the graph illustrates, approximately 92.5% relative humidity is achieved when a continuous flow rate of 35 liters/minute is delivered to the humidifier. A relative humidity of approximately 52.5% is achieved with a continuous flow rate of 125 liters/minute.

Because pulsing valve 30 only delivers an appropriate amount of water, as controlled by microprocessor 36, to blotting paper 50 to achieve the desired 28 to approximately 31 mg $H_2O/l$ gas at 37° C., not only is the gas delivered to the patient substantially free of particulate water droplets but no rainout is produced in tubing 18. In conventional humidifiers, after a sufficient amount of rainout occurs, the excess water in the inhalation tubing can result in water entering the lungs of the patient and thereby produce inappropriate lavage. Rainout is further eliminated by disposing humidifier 24 adjacent to the patient. Thus, the physical placement of humidifier 24 separate from reservoir 26 and adjacent to the patient allows the humidification system 10 to achieve the desired pure molecular humidity level without producing rainout. The pure molecular humidity produced with the humidification system is also not likely to cause nosocomial pneumonia or other humidifier related infections.

Figure 6:
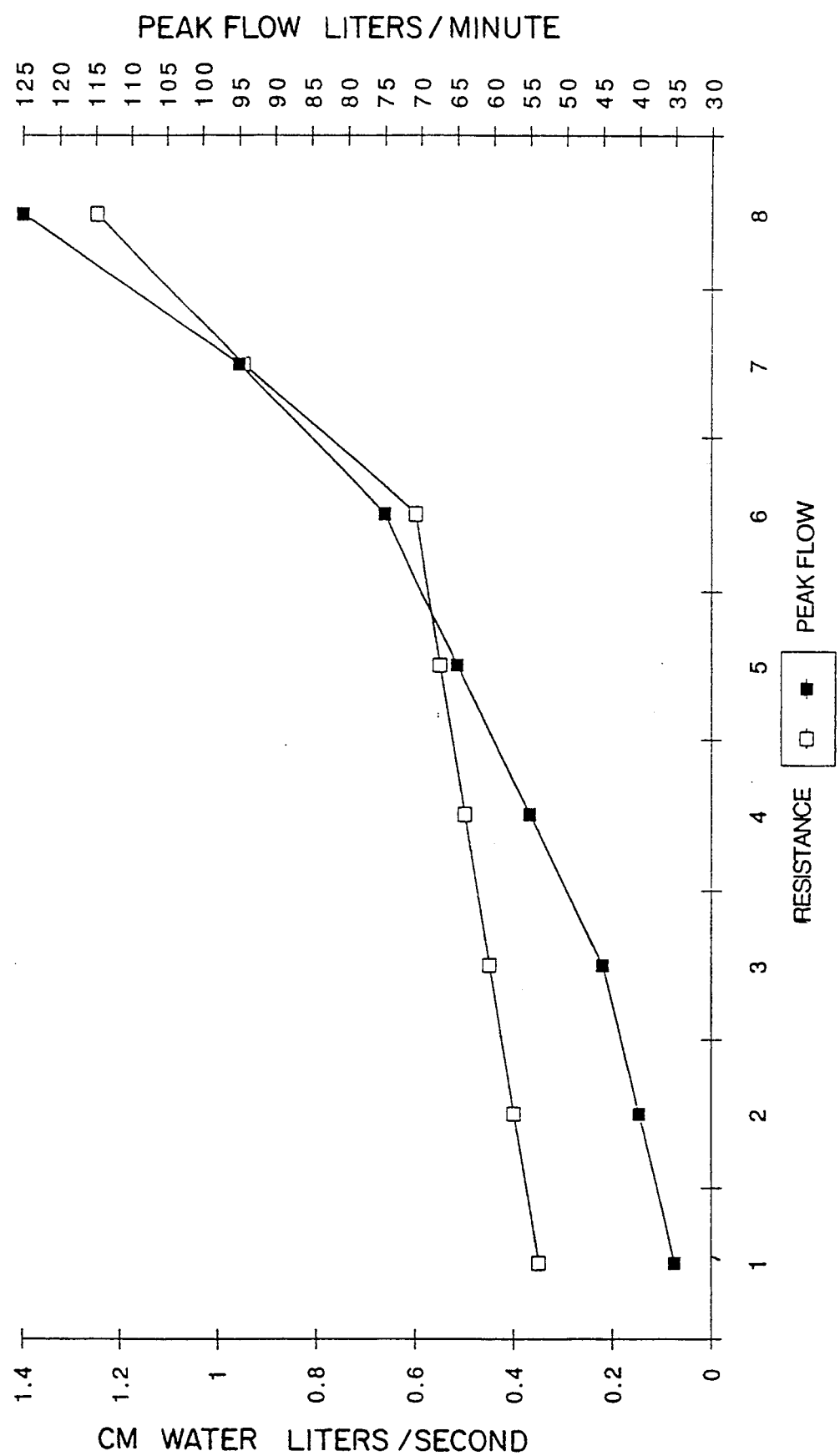
FIG. 6 is a graphical representation of inspiratory resistance in relationship to peak flow of a gas for a prototype of the humidification system of FIG. 1.

Because humidification system 10 does not produce rainout, inspiratory resistance is not increased significantly. FIG. 6 graphically illustrates inspiratory resistance in centimeters of water per liter per second in relationship to peak flow in liters per minute for the prototype of the humidification system 10.

Although the present invention has been described with reference to preferred embodiments, workers skilled in the art will recognize that changes may be made in form and detail without departing from the spirit and scope of the invention.

What is claimed is:

1. A humidification system for humidifying breathable gas supplied to a patient by a medical gas delivery device having inhalation tubing connecting from the device to provide a flow of gas to the patient and exhalation tubing extending from the patient, the system comprising:
 a humidifier comprising blotting paper to absorb the water and disposed in the path of flow of the inhalation tubing adjacent to the patient;
 delivery means for delivering water to the blotting paper;
 measurement means capable of measuring at least two parameters;
 a regulation means for regulating the delivery means based on the measured parameters so that an appropriate amount of water is delivered to the blotting paper to achieve a desired humidity level in the gas, said humidifier, said delivery means, said measurement means and said regulation means together providing a gas having a molecular humidity substantially free of particulate water droplets at a humidity level in the range from approximately 28 to approximately 31 mg $H_2O/l$ gas at approximately 37° C.

2. The humidification system according to claim 1 wherein a flow rate of gas supplied by the gas delivery device varies between 2 to 150 liters per minute.

3. The humidification system according to claim 1 wherein the delivery means comprises:
 a reservoir of water;
 piping that carries water from the reservoir to the humidifier; and a controllable pulsing valve disposed in the piping between the reservoir and the humidifier.

4. The humidification system according to claim 3 wherein the regulating means comprises a microprocessor that receives signals from the measurement means representative of the measured parameters and controls the pulsing valve in response to the signals.

5. The humidification system according to claim 1 wherein the measurement means comprises a temperature probe for measuring a temperature of the gas delivered to the patient.

6. The humidification system according to claim 1 wherein the measurement means comprises a flowmeter for measuring a flow rate of the gas supplied to the patient.

7. The humidification system according to claim 1 wherein the humidifier comprises a plurality of layers of blotting paper.

8. The humidification system according to claim 7 wherein the inhalation tubing is cylindrical having a known diameter and the layers of blotting paper are cylindrical having a substantially larger diameter than the diameter of the inhalation tubing.

9. The humidification system according to claim 8 wherein the layers of blotting paper comprise a multiplicity of holes allowing gas to more freely flow through the humidifier.

10. The humidification system according to claim 1 wherein the medical gas delivery device comprises a ventilator.

11. The humidification system according to claim 1 wherein the medical gas delivery device comprises an anesthesia circuit.

12. The humidification system according to claim 1 further comprising:
heating means for heating the humidifier.

13. A method of humidifying breathable gas being supplied to a patient by a ventilator or an anesthesia circuit, the method comprising:
directing the gas through substantially water saturated blotting paper;
delivering an amount of water to the blotting paper;
measuring at least two parameters; and
regulating the amount of water delivered to the blotting paper based on the measured parameters to achieve a desired humidity level in the gas, said steps of directing, delivering, measuring and regulating together providing a gas having a molecular humidity substantially free of particulate water droplets at a humidity level in the range from approximately 28 to approximately 31 mg $H_2O$/l gas at approximately 37° C.

14. The method according to claim 13 wherein the amount of water delivered to the blotting paper is limited with a controllable pulsing valve.

15. The method according to claim 14 further comprising:
sending signals representative of the measured parameters to a microprocessor; and
controlling the pulsing valve with the microprocessor in response to the signals.

16. The method according to claim 13 wherein the gas is directed through a plurality of layers of blotting paper.

17. The method according to claim 13 wherein the flow rate of a gas from the medical ventilator or anesthesia circuit varies between 2 to 150 liters per minute.

18. The method according to claim 13 wherein one of the measured parameters is a temperature of the gas delivered to the patient.

19. The method according to claim 13 wherein one of the parameters measured is a flow rate of the gas from the ventilator or anesthesia circuit.

20. The method according to claim 13 further comprising:
periodically heating the gas as the gas is directed through the blotting paper.

21. A humidification system for humidifying breathable gas supplied to a patient by a medical gas delivery apparatus having inhalation tubing connecting from the apparatus to the patient and exhalation tubing extending from the patient, the system comprising:
a humidifier disposed in the inhalation tubing adjacent to the patient;
a flow meter for measuring a flow rate of the gas supplied by the gas delivery apparatus;
a temperature probe for measuring a temperature of the gas delivered to the patient;
a reservoir of water;
piping carrying an amount of water from the reservoir to the humidifier;
a controllable pulsing valve disposed in the piping between the reservoir and the humidifier and capable of limiting the amount of water delivered to the humidifier, said humidifier, said flow meter, said temperature probe and said controllable pulsing valve together providing a gas having a molecular humidity substantially free of particulate water droplets at a humidity level in the range of from approximately 28 to approximately 31 mg $H_2O$/l gas at approximately 37° C.; and
a microprocessor receiving a temperature measurement signal from the temperature probe and a rate of flow signal from the flow meter, and controlling the pulsing valve in response to the received signals and thereby controlling the relative humidity of the gas delivered to the patient.

22. The humidification system according to claim 21 wherein the humidifier comprises a plurality of layers of blotting paper that absorb the water delivered from the reservoir of water.

* * * * *